United States Patent [19]

Ohyama et al.

[11] Patent Number: 4,822,814

[45] Date of Patent: Apr. 18, 1989

[54] NEW 1,3-DITHIOL-2-YLIDENE-ALKYLSULFONY-LACETATES AND THEIR USES

[75] Inventors: Hiroshi Ohyama, Chigasaki; Satoshi Hobara; Kazuyuki Tsujimoto, both of Atsugi; Shouji Tanaka, Hatano, all of Japan

[73] Assignee: Hokko Chemical Industry Co., Ltd., Tokyo, Japan

[21] Appl. No.: 26,205

[22] Filed: Mar. 16, 1987

[30] Foreign Application Priority Data

Mar. 19, 1986 [JP] Japan .................................. 61-59600

[51] Int. Cl.$^4$ .................. C07D 339/06; A61K 31/385
[52] U.S. Cl. ........................................ 514/440; 549/39
[58] Field of Search ......................... 549/39; 514/440; 426/132

[56] References Cited

U.S. PATENT DOCUMENTS 4,668,799 5/1987 Yoshizawa et al. .................. 549/39

*Primary Examiner*—Mary C. Lee
*Assistant Examiner*—Magrab
*Attorney, Agent, or Firm*—Larson and Taylor

[57] ABSTRACT

As new compound are provided alkyl 1,3-dithiol-2-ylidene-alkylsulfonylacetates which are useful as fungicidal agent and agent for therapeutically treating or preventing a liver disorder as well as agent for reducing the internal fat deposit or preventing excessive accumulation of the internal fat deposit in the body of animals, including humans. These new compounds have improved activities for these applications, as compared to known similar compounds.

6 Claims, No Drawings

NEW 1,3-DITHIOL-2-YLIDENE-ALKYLSULFONYLACETATES AND THEIR USES

SUMMARY OF THE INVENTION

This invention relates to novel 1,3-dithiol-2-ylidene sulfonylacetate derivatives. The new compounds of this invention have remarkably high activities as fungicidal agent of agricultural and horticultural utilities and also as therapeutic agents for treating therapeutically or preventing liver disorders. They also have activities as agent for reducing the internal fat, which acts to reduce the amounts of fat deposited in the interior of the body of animals, including humans, especially the amounts of fat accumulated and deposited in the abdominal cavity and flesh. More specifically, the compounds of this invention are useful as agents for reducing the amounts of the internal fat accumulated and deposited in animal bodies, which agents may usefully be administered to animals in order to reduce the amounts of the internal fat accumulated and deposited in the body of animals, for example, livestock animals such as cattle, poultry and cultivated fish, notably, the fat accumulated in their abdominal cavity or peritonea, for example, the amounts of the internal fat accumulated as fat layers deposited in or on internal organs such as the stomach and liver, the fat aggregates produced in such internal organs or the fat deposit accumulated in the flesh to be used as carcass, and/or in order to prevent such excessive accumulation of the internal fat.

BACKGROUND OF THE INVENTION

Some 1,3-dithiolene derivatives have been known to these dates. For example, U.S. Pat. No. 3,057,875 discloses that certain 2-methylene-4,5-dicyano-1,3-dithiolene derivatives represented by the following formula (i) are useful as ultraviolet absorbents:

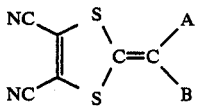

(i)

wherein A and B are individually a group =CN, —COOR or —SO$_2$R (R: alkyl group or the like), and the like.

It has also been disclosed in Japanese Patent Publication Nos. 18576/1981, 18577/1981, 18578/1981 and 18579/1981 (Corresponding to U.S. Pat. Nos. 4,080,467; 4,080,466; 4,022,907 and 4,035,387) that some other 1,3-dithiano derivatives represented collectively by the following general formula (ii) are useful as therapeutic agents for hepatopathy of human and animal:

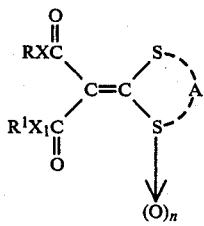

(ii)

wherein R and R$^1$ denote individually a lower alkyl group or an alkoxyethyl group; X and X$_1$ each denote oxygen or sulfur atom, n is an integer of 0, 1 or 2; and A means a group —CH$_2$—, —(CH$_2$)$_2$——(CH$_2$)$_3$—, —(CH$_2$)$_4$—, —CH=CH—or—CH(OR$_2$)—CH$_2$— where R$_2$ *acetyl or propionyl. In addition, the use of* 1,3-dithiano derivatives as fungicidal agents of agricultural and horticultural utilities is described in Japanese Patent Publication Nos. 34126/1972 and 34883/1976. Japanese Patent Application first publication "Kokai" No. 34852/1984 or U.S. Pat. No. 4,564,627 also discloses use of them as feed additives which reduce the amounts of the internal fat as accumulated and deposited in the abdominal cavity or peritonea of cattle, poultry, fish and the like and improve the eggshell strength of poultry.

The 1,3-dithiolene derivatives disclosed in the above-mentioned U.S. Pat. No. 3,057,875 do not show any physiological activities as agricultural chemicals and medicines. An object of this invention is to provide novel and useful 1,3-dithiano derivatives which are different from the known 1,3-dithiano derivatives and have remarkably useful activities as fungicidal agents of agricultural and horticultural applications and therapeutic agents for treating the hepatopathy. Another object of this invention is to provide 1,3-dithiano derivatives useful as excellent agents for reducing the internal fat of animals.

Some of the 1,3-dithiano derivatives described in the above-mentioned Japanese Patent Publication Nos. 34126/1972 and 34883/1976 have already found widespread utility as fungicidal agents for the control of rice blast (*Pyricularia oryzae*). When they are applied by the folier treatment, their controlling effects against rice blast (*Pyricularia oryzae*) may vary depending on environmental conditions and may not be able to provide steady, controlling effects in some instances.

In recent years, a feed of high-fat content and high-carbohydrate content is usually given in large amounts to cattle, poultry, cultivated fish, etc. so that they are caused to grow in shorter periods of time at small confined places under intensive care prior to their delivery to the market. As a result, fat tends to accumulate and deposit excessively in the bodies of these animals, especially, in their abdominal cavity or peritonea.

This means inefficiency in the conversion of nutrients in the feed given to animals into proteins which form edible meat parts of cattle and poultry. Carcass obtained from such animals having the excessively accumulated abdominal fat tends to have an unduly high fat content. This certainly does not meet the recent preference of consumers. More and more consumers are hence hesitant to buy the meat of high fat content obtained from the cattle, poultry and cultivated fish, which have been raised under such intensive care. This has led to a serious problem such as lowered demand.

When the known 1,3-dithiano derivatives described in the above-mentioned Japanese Patent Publication No. 18576/1981 through 18579/1981 and Japanese Patent Application first publication "Kokai" No. 34852/1984 (corresponding to U.S. Pat. No. 4,564,627) are administered to men as therapeutic agents for hepatopathy or are added to feed and administered to animals, some adverse effects may be given depending on the health conditions of animals or the manner of administration.

It is hence another object of this invention to solve the above-described problems in the various fields and to provide novel and highly-useful 1,3-dithiol-2-ylidene-alkylsulfonylacetic acid alkyl esters which can substitute for the known 1,3-dithiano derivatives.

DETAILED DESCRIPTION OF THE INVENTION

We, the present inventors, have synthetically prepared a number of 1,3-dithiol-2-ylidene sulfonylacetate derivatives and conducted an extensive investigation on their utility. As a result, we have succeeded in synthesizing new 1,3-dithiol-2-ylidene sulfonylacetate derivatives represented by the general formula (I):

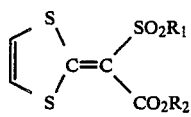

wherein $R_1$ and $R_2$ mean individually an alkyl group, namely, novel sulfonylacetate derivatives having a 1,3-dithiol-2-ylidene group at the β-position. We have then proceeded with a further investigation. As a result, we have now found that the new compounds of the general formula (I) can exhibit highly improved activity which are useful as fungicidal agent of agricultural and horticultural utilities and also as agent for treatment of liver disorders. We have further found that the new compounds of the general formula (I) can reduce the amounts of the internal fat accumulated in animals such as cattle, poultry and cultivated fish, especially, the amounts of the abdominal fat without impairing the growth of the animals and/or the new compound of the formula (I) can prevent excessive accumulation of the internal fat in the bodies of the animals when they are added to feed and administered to the animals together with the feed. Moreover, it has been uncovered that the new compounds of the formula (I) are also effective in improving the efficiency of conversion of feed into edible meat proteins and the quality of the carcass through the prevention of excessive accumulation of the internal fat.

According to the first aspect of this invention, therefore, there is provided a 1,3-dithiol-2-ylidene sulfonylacetate derivative represented by the general formula (I):

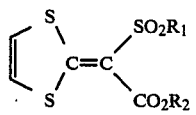

wherein $R_1$ and $R_2$ mean individually a lower alkyl group. The lower alkyl group for $R_1$ and $R_2$ may be selected from methyl, ethyl, n-propyl, iso-propyl, n-butyl, iso-butyl, tert-butyl, pentyl and hexyl.

Certain representative and specific examples of the compound (I) of this invention will next by shown in Table 1.

TABLE 1

| Compound No. | $R_1$ | $R_2$ | Melting point (°C.) |
|---|---|---|---|
| 1 | $CH_3$ | $CH_3$ | 166–168 (decomposed) |
| 2 | $CH_3$ | $C_2H_5$ | 134–136 |
| 3 | $CH_3$ | $i\text{-}C_3H_7$ | 127–127.5 |
| 4 | $C_2H_5$ | $CH_3$ | 121–122.5 |
| 5 | $C_2H_5$ | $C_2H_5$ | 72–73 |
| 6 | $i\text{-}C_3H_7$ | $i\text{-}C_3H_7$ | 124.5–125 |
| 7 | $CH_3$ | $n\text{-}C_3H_7$ | 141–142 |
| 8 | $CH_3$ | $n\text{-}C_4H_9$ | 87–88 |
| 9 | $C_2H_5$ | $n\text{-}C_4H_9$ | 99–100 |
| 10 | $n\text{-}C_3H_7$ | $CH_3$ | 133–135 |
| 11 | $n\text{-}C_3H_7$ | $C_2H_5$ | 103–104 |
| 12 | $i\text{-}C_3H_7$ | $CH_3$ | 141–142 |
| 13 | $i\text{-}C_3H_7$ | $C_2H_5$ | 99–101 |
| 14 | $i\text{-}C_3H_7$ | $n\text{-}C_3H_7$ | 78–79 |
| 15 | $i\text{-}C_3H_7$ | $n\text{-}C_4H_9$ | 67–69 |
| 16 | $n\text{-}C_4H_9$ | $CH_3$ | 85–86 |
| 17 | $n\text{-}C_4H_9$ | $C_2H_5$ | 79.5–81 |

Amongst the compounds of the formula (I) according to this invention, ethyl 1,3-dithiol-2-ylidene-isopropylsulfonyl acetate (Compound No. 13) and methyl 1,3-dithiol-2-ylidene-n-butylsulfonylacetate (Compound No.16) are most preferred.

The compounds (I) of this invention can be prepared by any of the following processes (a), (b) and (c):

Process (a):

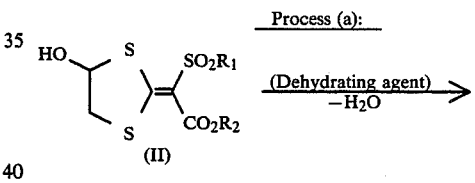

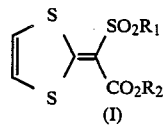

where $R_1$ and $R_2$ have the same meaning as defined above.

The compound (I) of this invention can be obtained by dehydrating a corresponding hydroxydithiolane represented by the general formula (II) above. The dehydration reaction is generally conducted by reacting a dehydrating agent with the compound of the formula (II) in an inert solvent. As suitable substances having the dehydrating actions, there are acids, acid anhydrides and like materials which are employed usually for that purpose. In addition, it is also possible to use such a halogenating agent which halogenates the hydroxyl group, and then form the double bond by the dehydrohalogenation. Illustrative examples of the dehydrating agent suitable for this purpose may include sulfuric acid, hydrochloric acid, phosphoric acid, potassium hydrogen phosphate, chlorosulfonic acid, methanesulfonyl chloride, benzenesulfonyl chloride, phosphorus pentoxide, thionyl chloride, phosphorus trichloride, phosphorus oxytrichloride, phosphorus pentachloride, etc. Where an acid or acid anhydride is used as a dehydrating agent, its amount may vary from a catalytic amount to an equimolar amount, depending on the kind of the acid or acid anhydride. The amount of the dehydrating agent may be adjusted suitably in accordance with the state of progress of the reaction. In the case of using a halogenating agent, the halogenating agent may usually be used in an equimolar amount or in a somewhat excessive amount and reacted with the compound (II), followed by reacting a base such as sodium hydroxide, potassium hydroxide, pyridine or triethylamine with the resulting halogenation product. As the inert solvent for the reaction medium, it is possible to use a hydrocarbon such as benzene or toluene, a halogenated hydrocarbon such as dichloromethane, chloroform or carbon tetrachloride, an ether such as ethyl ether or tetrahydrofuran, and the like. The reaction temperature may be set at any desired level ranging from the room temperature to the boiling point of a solvent. In general, however, it is chosen from a range of from room temperature to about 80° C. After completion of the reaction, water and an organic solvent are added to the reaction mixture and the organic layer is separated to give an organic solution of the intended product of the formula (I). When a halogenating agent is used as a dehydrating agent in the above dehydrating reaction, the intended product of the formula (I) can also be produced by isolating such intermediate, halogenation product in which the hydroxyl group has been substituted by a halogen atom, and then dehydrohalogenating the intermediate product isolated. Production of certain compounds of formula (I) by the process (a) will be illustrated by Examples 1, 2, 5, 6 and 7 given hereinafter.

Incidentally, the compounds of formula (II) useful in the practice of the above process (a) are novel. They can readily be prepared by using as starting materials their corresponding alkyl sulfonylacetates, which are known compounds, and processing them in a manner similar to that known per se in the art. Illustrative preparation of certain compounds of formula (II) will also be described in Referential Preparation Examples 1 and 2 given later.

Process (b):

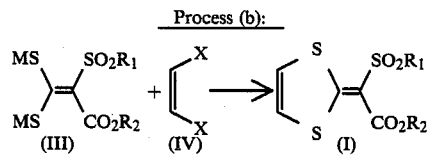

wherein M means an alkali metal, X denotes a halogen atom and both Xs may be either the same or different, and $R_1$ and $R_2$ have the same meaning as defined above.

The compounds of formula (I) of this invention can also be produced by reacting a dialkali metal salt of the corresponding ketene mercaptal of the general formula (III) as above with a cis-1,2-dihalogenated ethylene of formula (IV). The latter reactant compounds of formula (IV) are known in the art. The reaction is conducted generally in an aprotonic polar solvent, which may be dimethylformamide, dimethylsulfoxide or the like. The reaction temperature may be chosen from room temperature to 100° C., preferably, from room temperature to 80° C. After completion of the reaction, an organic solvent such as benzene or chloroform is added along with water to the reaction mixture and the organic layer is separated to afford an organic solution of the intended product of formula (I). Preparation of certain compounds of formula (I) by the process (b) will be illustrated with reference to Examples 3 and 8–12 given hereinafter.

The compound of formula (III) useful in the practice of the above process (b) can be prepared by reacting a corresponding alkyl sulfonylacetate with carbon disulfide in the presence of an alkali metal base in an aprotonic polar solvent. Without isolation of the compounds (III) from the reaction solvent, the compound (III) as prepared may usually be employed directly as starting materials for the process (b), Process (c):

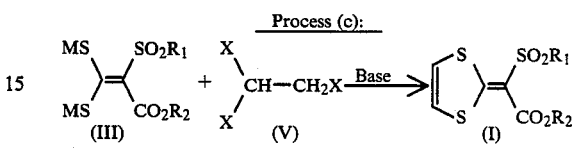

wherein M, X, $R_1$ and $R_2$ have the same meaning as defined above.

The compounds (I) of this invention can be produced by reacting a dialkali metal salt of a corresponding ketene mercaptal with a 1,1,2-trihalogenated ethane of formula (V) as above in the presence of a base. The reaction is generally conducted in an aprotonic polar solvent, which may be dimethylformamide, dimethylsulfoxide or the like. The reaction temperature may be chosen from room temperature to 100° C., preferably, from room temperature to 80° C. As the base for this purpose may usually be employed a base containing the same alkali metal as the corresponding compound (III), and the base may be for example, sodium hydroxide or potassium hydroxide. The post treatment of the reaction solution may be carried out in the same manner as in the process (b). Similarly to the process (b), the compounds (III) are used without their isolation. Illustrative preparation of some compounds of formula (I) by the process (c) will be described subsequently in Examples 4 and 13–15 given later.

The compounds of this invention represented by the general formula (I) have been found to exhibit high fungicidal activities and therapeutic activities for the hepatopathy as mentioned above. Their applications in these fields will hereinafter be described.

In order to use the compounds of this invention as fungicidal agent of agricultural and horticultural utilities, they are formulated into wettable powder, oil preparations, liquid preparations, emulsifiable concentrates, sol (flowable) preparations, dust, DL (driftless) dust, fine granules, granules or the like by using the active compound as such, or diluting them with a liquid carrier such as an organic solvent, solid powder carrier or any other suitable carrier, optionally along with an auxiliary agent such as wetting agent, spreader, dispersant, emulsifier or sticking agent as needed. As exemplary liquid carriers usable upon formulation of the compounds into their preparations, may be used solvents such as water, aromatic hydrocarbons, aliphatic hydrocarbons, alcohols, esters, ketones, acid amides and dimethylsulfoxide. Illustrative examples of the solid carrier may include mineral powder such as clay, talc, kaolin, bentonite, diatomaceous earth, calcium carbonate and silicic acid, and organic powder such as wood powder, etc. As an auxiliary agent, may be employed a surfactant such as non-ionic, anionic, cationic or ampholytic surfactant, or a binder such as lignin-sulfonic acid or a salt thereof, gum, fatty acid salt, methylcellulose or the like.

According to the second aspect of this invention, therefore, there is provided a fungicidal composition for agricultural and horticultural utility, comprising, as an active ingredient, a 1,3-dithiol-2-ylidene sulfonylacetate derivative represented by the general formula

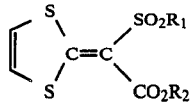

(I)

wherein $R_1$ and $R_2$ are each a lower alkyl group, in combination with a solid or liquid carrier for the active ingredient.

Preparations such as wettable powder, soluble concentrates and emulsifiable concentrates may each contain the active ingredient in an amount of 1–95 wt.%, generally, 2–75 wt.%. These preparations may be diluted with water, usually, to concentrations of the active ingredient of 0.0001–10 wt. % upon their use. Preparations in the form of dust or granules may generally contain 0.1–10 wt. % of the active ingredient. While, concentrated formulations such as oil preparations, emulsifiable concentrates and sol (flowable) preparations may be applied to the fields as ultra-low-volume spraying preparations without being diluted.

Regarding the procedures for formulation of the compounds (I) of this invention into agricultural and horticultural fungicidal compositions, illustrative formulations containing of certain compounds of this invention will next be described. Needless to say, the present invention is not limited to or by the following Formulation Examples, in which all designations of "part" or "parts" are given in part by weight or parts by weight.

FORMULATION EXAMPLE 1: WETTABLE POWDER

A wettable powder containing 20% of Compound No. 5 (see Table 1 given hereinbefore) as an active ingredient was obtained by uniformly grinding and mixing together 20 parts of Compound No.5, 5 parts of polyoxyethylene alkylaryl ether, 3 parts of calcium ligninsulfonate and 72 parts of diatomaceous earth.

FORMULATION EXAMPLE 2: EMULSIFIABLE CONCENTRATE

An emulsion containing 30% of Compound No. 6 (see Table 1) as an active ingredient was obtained by mixing 30 parts of Compound No. 6, 50 parts of xylene and 20 parts of polyoxyethylene alkylaryl ether together into a uniform mixture.

FORMULATION EXAMPLE 3: OIL PREPARATION

An oil preparation containing 50% of Compound No. 4 as an active ingredient was obtained by mixing 50 parts of Compound No. 4 and 50 parts of ethyl cellosolve together into a uniform solution.

FORMULATION EXAMPLE 4: SOL (FLOWABLE) PREPARATION

A sol preparation containing 40% of Compound No. 1 as an active ingredient was obtained by uniformly mixing together 40 parts of Compound No. 1, which had been ground to particle size of 10 μm or smaller, 2 parts of lauryl sulfate, 2 parts of sodium alkylnaphthalenesulfonate, 1 part of hydroxypropylcellulose and 55 parts of water.

FORMULATION EXAMPLE 5: DUST PREPARATION

A dust preparation containing 1% of Compound No. 2 as an active ingredient was obtained by uniformly mixing and grinding together 0.5 parts of Compound No. 2, 0.5 parts of fine powder of anhydrous silicic acid, 0.5 parts of calcium stearate, 50 parts of clay and 48.5 parts of talc.

FORMULATION EXAMPLE 6: GRANULAR PREPARATION

A granular preparation containing 3% of Compound No. 1 was prepared by uniformly mixing and grinding together 3 parts of Compound No. 1, 1 part of calcium ligninsulfonate, 30 parts of bentonite and 66 parts of clay, adding water to the mixture and granulating the resultant wet mixture, drying the resultant granules and then seeving the same.

Furthermore, in order to use the compounds of formula (I) according to this invention as the therapeutic agents for hepatopathy on the other hand, the compounds of this invention may be administered as such. As alternative, the compounds of this invention may be mixed with an excipient and one or more other physiologically active substances into mixtures by methods known commonly in the art. As a further alternative, they may also be formulated into units of prescribed doses. Exemplary dosage forms as medicines may include powder, granules, tablets, sugarcoated tablets, capsules, pills, suspensions, solutions, emulsions, ampouled parenteral solutions, isotonic solutions, etc.

The excipient should be such one that is pharmaceutically acceptable. It may be solid, semi-solid, liquid or capsules.

For the treatment of hepatopathy, the compounds of this invention can be administered either orally or parenterally to men and animals by usual methods known per se in the art.

According to a further aspect of this invention, therefore, there is provided a pharmaceutical composition for therapeutic treatment or prevention of a liver disorder, comprising, as an active ingredient, an effective amount of a 1,3-dithiol-2-ylidene sulfonylacetate derivative represented by the general formula

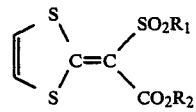

(I)

wherein $R_1$ and $R_2$ are each a lower alkyl group, optionally in combination with a pharmaceutically as acceptable carrier for the active ingredient. According to this invention, there is further provided a method for therapeutically treating or preventing a liver disorder of animals, including humans, which comprises orally or parenterally administering to said animal in need of the therapy or prevention, an effective amount of a compound represented by the general formula (I) as defined above.

In order to obtain effective results for the hepatopathy by administration of the new compound of this invention to animals, the effective daily dose may advantageously be 0.1 mg–500 mg of an active ingredient per Kg of the body weight upon oral administration and 0.01–250 mg of an active ingredient per Kg of the body weight upon parenteral administration.

When administered to men, the effective daily dose may advantageously be 0.1–250 mg per Kg of the body weight upon oral administration and 0.01–100 mg per Kg of the body weight upon parenteral administration in view of the difference in sensitivity, safety, etc. based on the effective dose for animals.

Illustrative dosage forms of certain compounds of this invention as therapeutic agents for hepatopathy will next be described. Needless to say, the present invention is not limited to or by the following Formulation Examples, in which all designations of "part" or "parts" are given in part by weight or parts by weight.

FORMULATION EXAMPLE 7: POWDER

Powder containing 10% of Compound No. 1 (see Table 1) as an active ingredient was obtained by uniformly mixing 10 parts of Compound No. 1, 10 parts of heavy-grade magnesium oxide and 80 parts of lactose together into powder or particles.

FORMULATION EXAMPLE 8: GRANULES

Granules containing 50% of Compound No. 2 as an active ingredient were obtained by uniformly mixing and kneading 50 parts of Compound No.2, 10 parts of starch, 15 parts of lactose, 20 parts of crystalline cellulose, 5 parts of polyvinyl alcohol and 30 parts of water, grinding and granulating the resultant mixture, and then drying the resultant granules.

FORMULATION EXAMPLE 9: TABLETS

Tablets containing 50% of Compound No. 6 as an active ingredient were obtained by uniformly mixing and kneading 50 parts of Compound No. 6, 10 parts of starch, 15 parts of lactose, 20 parts of crystalline cellulose, 4 parts of polyvinyl alcohol, 1 part of calcium stearate and 30 parts of water, grinding the resultant mixture, drying the resultant powder and then compressing and forming the thus-dried powder.

FORMULATION EXAMPLE 10: PARENTERAL SOLUTION

A parenterally injectable solution containing 0.5% of Compound No. 3 as an active ingredient was obtained by mixing 0.5 parts of Compound No. 3, 2.5 parts of a nonionic surfactant and 97 parts of physiological saline under heating, and sterilizing the resultant solution,

FORMULATION EXAMPLE 11: CAPSULES

Capsules were obtained by uniformly mixing 10 parts of Compound No. 4, 10 parts of synthetic aluminum silicate, 5 parts of potassium hydrogenphosphate and 75 parts of lactose into powder or particles and then filling the powder or particles in commerically available capsule shells.

Preparation of certain compounds of formula (I) according to this invention will hereinafter be illustrated with reference to the following Examples.

EXAMPLE 1

Preparation of ethyl 1,3-dithiol-2-ylidenemethylsulfonylacetate (Compound No. 2) [by Process (a)]

A mixture of 28,4 g of ethyl 4-hydroxy-1,3-dithiol-2-ylidene-methylsulfonylacetate, 1 g of p-toluenesulfonic acid and 100 ml of benzene was subjected to azeotropic distillation and the dehydration reaction for 3 hours while stirring the mixture under reflux. After cooling, water was added to the reaction solution and the resultant organic layer was separated. The solvent was distilled off under reduced pressure to afford 24.2 g of the title compound as pale brown crystals. Upon recrystallization from ethanol, they turned to white crystals. Melting point: 134°–136° C.

EXAMPLE 2

Preparation of isopropyl 1,3-dithiol-2-ylideneisopropylsulfonylacetate (Compound No. 6) [by Process (a)]

After dropwise addition of 13.5 g of thionyl chloride to a mixture of 32.7 g of 4-hydroxy-1,3-dithiol-2-ylidene-isopropylsulfonylacetate and 100 ml of benzene, the reaction mixture was refluxed for 30 minutes. Subsequent to its cooling, 13.0 g of triethylamine was added to the reaction solution, followed by further reflux for 3 hours. The resultant reaction mixture was cooled. Water was added to the reaction mixture and the resulting organic layer was separated. Upon removal of the solvent by distillation under reduced pressure, 28.3 g of the title compound was obtained as pale brown crystals. Upon recrystallization from a mixed solvent of benzene and n-hexane, they turned to white crystals. Melting point: 124.5°–125° C.

REFERENTIAL PREPARATION EXAMPLE 1:

Preparation of ethyl 4-hydroxy-1,3-dithiol-2ylidene-methylsulfonylacetate [the starting compound for the preparation of Compound No. 2 of this invention; a compound represented by the general formula (II)]

After dissolving 16.6 g of ethyl methylsulfonylacetate in 150 ml of dimethylformamide, 11.2 g of potassium hydroxide was added to the solution. The reaction mixture was stirred for 1 hour at room temperature, followed by a dropwise addition of 19.6 g of chloroacetoaldehyde (a 40% aqueous solution) under ice-cooling. The resulting mixture was then stirred for 2 hours at room temperature. After adding concentrated hydrochloric acid to the reaction mixture and neutralizing the same, the dimethylformamide was distilled off from the mixture under reduced pressure. Chloroform and water were added to the residue and the resulting chloroform layer was collected. Upon removal of the solvent by distillation under reduced pressure, 25.6 g of the title compound was obtained as brown crystals, which gave white crystals upon recrystallization from chloroform/n-hexane. Melting point: 145°–147° C.

EXAMPLE 3:

Preparation of methyl 1,3-dithiol-2-ylidenemethylsulfonylacetate (Compound No. 1) [by Process (b)]

To a mixture of 15.2 g of methyl methylsulfonylacetate, 7.6 g of carbon disulfide and 200 ml of dimethylformamide, 14.0 g of potassium hydroxide was added under ice-cooling. The resultant mixture was stirred for 3 hours. Thereafter, 9.7 g of cis-1,2-dichloroethylene was added, followed by stirring at 80° C. for 4 hours. After cooling the reaction mixture, chloroform and water were added and the resulting organic layer was separated. Upon removal of the solvent by distillation under reduced pressure, 20.9 g of the title compound was obtained as pale yellow crystals. Upon recrystallization from a mixed solvent of chloroform and n-hexane, they turned to white crystals. Melting point: 166°–168° C. (decomposed).

EXAMPLE 4:

Preparation of isopropyl 1,3-dithiol-2-ylidenemethylsulfonylacetate (Compound No. 3) [by Process (c)]

To a mixture of 18 g of isopropyl methylsulfonylacetate, 7.6 g of carbon disulfide and 200 ml of dimethylformamide, 22.4 g of potassium hydroxide was added under ice-cooling. The resultant mixture was stirred for 2 hours. Thereafter, 13.3 g of 1,1,2-trichloroethane was added, followed by stirring at 80° C. for 3 hours. After cooling the reaction mixture, chloroform and water were added and the resulting organic layer was separated. Upon removal of the solvent by distillation under reduced pressure, 24.1 g of the title compound was obtained as pale yellow crystals. Upon recrystallization from isopropanol, they turned to white crystals. Melting point: 127°–127.5° C.

EXAMPLE 5:

Preparation of n-propyl 1,3-dithiol-2-ylidenemethylsulfonylacetate (Compound No. 7) [by Process (a)]

A mixture of 29.8 g of n-propyl 4-hydroxy-1,3-dithiol-2-ylidene-methylsulfonylacetate, 1 g of paratoluenesulfonic acid and 100 ml of benzene was subjected to azeotropic distillation and the dehydration reaction for 3 hours while stirring the mixture under reflux. After cooling, water was added to the mixture and the resultant organic layer was separated. The solvent was distilled off from the organic solution under reduced pressure to yield 25.8 g of the title compound as pale brown crystals. Upon recrystallization from n-propanol, they turned to white crystals. Melting point: 141°–142° C.

EXAMPLE 6:

Preparation of n-butyl 1,3-dithiol-2-ylideneethylsulfonylacetate (Compound No. 9) [by Process (a)]

The process of Example 5 was repeated using 32.6 g of n-butyl 4-hydroxy-1,3-dithiol-2-ylidene-ethylsulfonylacetate, and 28.1 g of the titled compound was obtained as pale yellow crystals. Upon recrystallization from a mixed solvent of benzene and n-hexane, they turned to white crystals. Melting point: 99°–100° C.

EXAMPLE 7:

Preparation of methyl 1,3-dithiol-2-ylidenen-butyl-sulfonylacetate (Compound No. 16) [by Process (a)]

The process of Example 5 was repeated using 31,2 g of methyl 4-hydroxy-1,3-dithiol-2-ylidene-n-butyl-sulfonylacetate, and 27.1 g of the title compound was obtained as pale yellow crystals. Upon recrystallization from methanol, they turned to white crystals. Melting point: 85°–86° C.

REFERENTIAL PREPARATION EXAMPLE 2:

Preparation of n-propyl 4-hydroxy-1,3-dithiol2-ylidene-methylsulfonylacetate [the starting compound for the preparation of Compound No. 7 of this invention; a compound represented by the general formula (II)]

After dissolving 18.0 g of n-propyl methylsulfonylacetate in 150 ml of dimethylformamide, 11.2 g of potassium hydroxide was added to the solution, followed by stirring for 1 hour at room temperature. Thereafter, 196 g of chloroacetaldehyde (a 40% aqueous solution) was added dropwise under ice-cooling and the resulting mixture was stirred for 2 hours at room temperature. Concentrated hydrochloric acid was added to the reaction mixture to neutralize the same, followed by removal of the dimethylformamide by distillation under reduced pressure. Chloroform and water were added to the residue and the resulting chloroform layer was separated. Upon removal of the solvent from the organic solution by distillation under reduced pressure, 27.5 g of the title compound was obtained in the form of an oily substance. It was purified by chromatography on a silica gel column. $n_D^{23} = 1.5973$.

EXAMPLE 8:

Preparation of ethyl, 1,3-dithiol-2-ylideneisopropylsulfonylacetate (Compound No. 13) [by Process (b)]

To a mixture of 19.4 g of ethyl isopropylsulfonylacetate, 7.6 g of carbon disulfide and 200 ml of dimethylformamide, 14.0 go of potassium hydroxide was added under ice-cooling. The resultant mixture was stirred for 3 hours. Thereafter, 9.7 g of cis-1,2-dichloroethylene was added to the mixture, followed by stirring at 80° C. for 4 hours. After cooling the reaction mixture, chloroform and water were added and the resulting organic layer was separated. Upon removal of the solvent from the organic solution by distillation under reduced pressure, 27.4 g of the title compound was obtained as pale yellow crystals. Upon recrystallization from a mixed solvent of chloroform and n-hexane, they turned to white crystals. Melting point: 99°–101° C.

EXAMPLE 9:

Preparation of n-butyl 1,3-dithiol-2-ylidenemethylsulfonylacetate (Compound No. 8) [by Process (a)]

The process of Example 8 was repeated using 19.4 g of n-butyl methysulfonylacetate, and 26.8 g of the title compound was obtained as pale brown crystals. Upon recrystallization from a mixed solvent of chloroform and n-hexane, they turned to white crystals. Melting point: 87°–88° C.

EXAMPLE 10:

Preparation of ethyl 1,3-dithiol-2-ylidenen-propylsulfonylacetate (Compound No. 11) [by Process (b)]

The process of Example 8 was repeated using 19.4 g of ethyl n-propylsulfonylacetate, and 26.5 g of the title compound was obtained as pale yellow crystals. Upon recrystallization from ethanol, they turned to white crystals. Melting point: 103°–104° C.

EXAMPLE 11:

Preparation of methyl 1,3-dithiol-2-ylideneisopropylsulfonylacetate (Compound No. 12) [by Process (b)]

The process of Example 8 was repeated using 18.0 g of methyl isopropylsulfonylacetate, and 24.4 g of the title compound was obtained as brown crystals. Upon recrystallization from methanol, they turned to white crystals. Melting point: 141°–142° C.

EXAMPLE 12:

Preparation of n-butyl 1,3-dithiol-2-ylideneisopropylsulfonylacetate (Compound No. 15) [by Process (b)]

The process of Example 8 was repeated using 22.2 g of n-butyl isopropylsulfonylacetate, and 28.7 g of the title compound was obtained as pale brown crystals. Upon recrystallization from a mixed solvent of chloroform and n-hexane, they turned to white crystals. Melting point: 67°–69° C.

EXAMPLE 13:

Preparation of methyl 1,3-dithiol-2-ylidenen-propylsulfonylacetate (Compound No. 10) [by Process (c)]

To a mixture of 18.0 g of methyl n-propylsulfonylacetate, 7.6 g of carbon disulfide and 200 ml of dimethylformamide, 22.4 g of potassium hydroxide was added under ice-cooling. The resultant mixture was stirred for 2 hours. Thereafter, 13.3 g of 1,1,2-trichloroethane was added to the reaction mixture, followed by stirring at 80° C. for 3 hours. After cooling the reaction mixture, chloroform and water were added and the resulting organic layer was separated. Upon removal of the solvent by distillation under reduced pressure, 25.2 g of the title compound was obtained as pale yellow crystals. Upon recrystallization from methanol, they turned to white crystals. Melting point: 133°–135° C.

EXAMPLE 14:

Preparation of n-propyl 1,3-dithiol-2-ylideneisopropylsulfonylacetate (Compound No. 14) [by Process (c)]

The process of Example 13 was repeated using 20.8 g of n-propyl isopropylsulfonylacetate, and 27.4 g of the title compound was obtained as pale yellow crystals. Upon recrystallization from n-propanol, they turned to white crystals. Melting point: 78°–79° C.

EXAMPLE 15:

Preparation of ethyl 1,3-dithiol-2-ylidenen-butylsulfonylacetate (Compound No. 17) [by Process (c)]

The process of Example 13 was repeated using 20.8 g of ethyl n-butylsulfonylacetate, and 28.1 g of the title compound was obtained as pale brown crystals. Upon recrystallization from ethanol, they turned to white crystals. Melting point: 79.5°–81° C.

Now, in order to demonstrate the usefulness of the compounds of formula (I) of this invention as fungicidal agents and the aforementioned medicines, Tests 1–3 are shown below.

TEST 1:

Test on the controlling effects against rice blast (Pyricularia oryzae)

Rice seedlings (3 leaf stage, species: Asahi) as soil-cultured in an unglazed pot of 9 cm across in a greenhouse were sprayed with a test solution containing the active ingredient at a prescribed concentration, which was prepared by diluting with water a wettable powder as prepared in accordance with the procedure of Formulation Example 1. The rice seedlings so treated were then maintained overnight under wet room conditions (humidity: 95–100%, temperature: 24°–25° C). One day after the spraying, the rice plants were sprayed and inoculated with a spore suspension of *Pyricularia oryzae*. Five days after the inoculation, the number of lesions infected by *Pyricularia oryzae* per leaf of the third leave was counted, and the control value (%) was calculated in accordance with the below-given equation. In addition, the phytotoxicity to rice seedlings was also estimated in accordance with the scales given below. The test was conducted in three replicates using three pots of rice seedlings as a group for each concentration. The averaged control value was evaluated. Results are summarized in Table 2. The scales for estimation of the phyto-toxicity were employed equally in the next Test.

$$\text{Control value}(\%) = \left( 1 - \frac{\text{Number of rice blast lesions in sprayed group}}{\text{Number of rice blast lesions in non-sprayed group}} \right) \times 100$$

TABLE 2

Control Effects against Rice Blast (*Pyricularia Oryzae*)

| Compound No. | Concentration of active ingredient in the sprayed solution (ppm) | Control value (%) | Phyto-toxicity |
|---|---|---|---|
| 1 | 200 | 96 | 0 |
| 2 | 200 | 96 | 0 |
| 3 | 200 | 98 | 0 |
| 4 | 200 | 95 | 0 |
| 5 | 200 | 94 | 0 |
| 6 | 200 | 92 | 0 |
| 7 | 200 | 94 | 0 |
| 8 | 200 | 92 | 0 |
| 9 | 200 | 94 | 0 |
| 10 | 200 | 96 | 0 |
| 11 | 200 | 94 | 0 |
| 12 | 200 | 94 | 0 |
| 13 | 200 | 98 | 0 |
| 14 | 200 | 95 | 0 |
| 15 | 200 | 94 | 0 |
| 16 | 200 | 98 | 0 |
| 17 | 200 | 96 | 0 |
| Comparative Chemical A | 200 | 0 | 1 |
| Comparative Chemical B | 200 | 72 | 0 |
| Comparative Chemical C | 200 | 63 | 0 |
| Comparative Chemical D | 480 | 69 | 0 |
| Non-treated | — | 0 | — |

TABLE 2-continued

Control Effects against Rice Blast (*Pyricularia Oryzae*)

| Compound No. | Concentration of active ingredient in the sprayed solution (ppm) | Control value (%) | Phyto-toxicity |
|---|---|---|---|
| group | | | |

Scales for phyto-toxicity:
5: Very severe
4: Severe
3: Substantial
2: Some
1: Slight
0: None Comparative Chemical A:

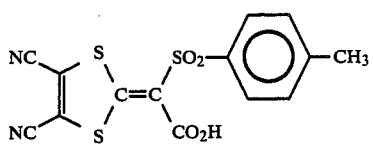

(prepared newly by the present inventors with deducing from claims 1 of U.S. Patent No. 3,057,875)

Comparative Chemical B:

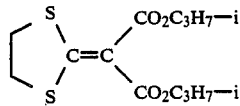

(Described in Japanese Patent Publication No. 34126/1972).

Comparative Example C:

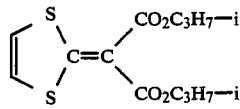

(Described in Japanese Patent Publication No. 34883/1976). Comparative Chemical D:

O,O-Diisopropyl S-Benzylthiophosphate (IBP emulsifiable Concentrate).

TEST 2:

Test on the control effects against cucumber powdery mildew (Sphaerotheca fuliginea)

Cucumber seedlings (1 leaf stage, species: Sagami Hanjiro) as soil-cultured in a glazed pot of 9 cm across in a greenhouse were sprayed with 10 ml of a chemical solution containing the active ingredient at a prescribed concentration, which was prepared by diluting with water an emulsifiable concentrate as formulated in accordance with the procedure of Formulation Example 2. After allowing the treated cucumber seedlings to sand overnight, the plants were sprayed and inoculated with a spore suspension of *Sphaerotheca fuliginea*. Ten days after the inoculation, the percent area of lesions infected by *Sphaerotheca fuliginea* was evaluated and the control value (%) was then calculated in accordance with the belowgiven equation. Results are summarized in Table 3.

$$\text{Control value}(\%) = \left(1 - \frac{\text{Number of the disease lesions in sprayed group}}{\text{Number of the disease lesions in non-sprayed group}}\right) \times 100$$

TABLE 3

Control Effects against Cucumber Powdery Mildew (*Sphaerotheca fuliginea*)

| Compound No. | Concentration of active ingredient in sprayed solution (ppm) | Control value (%) | Phyto-toxicity |
|---|---|---|---|
| 1 | 100 | 96 | 0 |
| 2 | 100 | 98 | 0 |
| 3 | 100 | 94 | 0 |
| 4 | 100 | 92 | 0 |
| 5 | 100 | 94 | 0 |
| 6 | 100 | 91 | 0 |
| 7 | 100 | 92 | 0 |
| 8 | 100 | 94 | 0 |
| 9 | 100 | 96 | 0 |
| 10 | 100 | 92 | 0 |
| 11 | 100 | 96 | 0 |
| 12 | 100 | 96 | 0 |
| 13 | 100 | 98 | 0 |
| 14 | 100 | 91 | 0 |
| 15 | 100 | 92 | 0 |
| 16 | 100 | 96 | 0 |
| 17 | 100 | 96 | 0 |
| Comparative Chemical A | 100 | 0 | 2 |
| Comparative Chemical B | 100 | 0 | 0 |
| Comparative Chemical C | 100 | 0 | 0 |
| Comparative Chemical E | 100 | 83 | 0 |
| Non-treated group | — | 0 | — |

Comparative Chemical E: 6-Methylquinoxaline-2,3-dithiocarbonate (Quinoxaline-type wettable powder)

TEST 3:

Test on the medicinal effects of inhibiting liver disorder

Each test compound was either dissolved or suspended in olive oil and was forcedly and orally administered once at a dose of 250 mg/kg to rates (7-weeks-aged, SD-strain, male, five in each group). Three hours later, carbon tetrachloride was orally administered at a rate of 0.5 ml/kg to the rates in the same manner. Upon an elapse of 24 hours after the administration of carbon tetrachloride, the rates were discussed. The degree of liver damage invoked of each rate under test was visually estimated to obtain the index of liver damage.

In addition, blood sample was collected at the time of the dissection. Plasma was then obtained from the blood by centrifugal separation. The activity of an enzyme, GPT, in the plasma were measured by the Reitmen-Frankel method and the GPT activity was expressed in terms of Karmen unit. Results are given in Table 4.

| Index of liver damage | State of liver |
|---|---|
| 0 | No damage (normal) |
| 1 | Slightly damaged |
| 2 | Apparently damaged |
| 3 | Severe damage |

TABLE 4

| | Inhibitory Effects against liver damage | |
|---|---|---|
| Compound No. | Liver damage index | GPT value of plasma |
| 1 | 0.6 | 25 |
| 2 | 0.6 | 27 |
| 3 | 0.8 | 42 |
| 4 | 0.6 | 28 |
| 5 | 0.6 | 26 |
| 6 | 0.8 | 45 |
| 7 | 0.6 | 27 |
| 8 | 0.6 | 27 |
| 9 | 0.8 | 33 |
| 10 | 0.6 | 29 |
| 11 | 0.6 | 28 |
| 12 | 0.8 | 32 |
| 13 | 0.6 | 24 |
| 14 | 0.6 | 26 |
| 15 | 0.6 | 28 |
| 16 | 0.6 | 24 |
| 17 | 0.8 | 34 |
| Comparative Chemical A | 2.8 | 196 |
| Comparative Chemical B | 1.4 | 79 |
| Comparative Chemical C | 1.2 | 63 |
| Comparative Chemical F | 1.7 | 102 |
| Comparative Chemical G | 1.9 | 138 |
| Comparative Chemical H | 1.8 | 114 |
| CCl4 alone | 2.8 | 183 |
| Non-treated group | 0 | 21 |

Comparative Chemicals A, B and C: see Tables 2 and 3.

Comparative Chemical F:

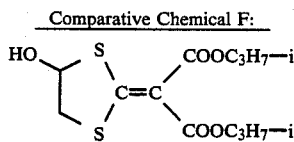

(Described in Japanese Patent Publication No. 18577/1981). Comparative Chemical G:

Comparative Chemical G:

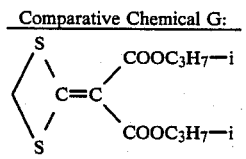

(Described in Japanese Patent Publication No. 18578/1981).

Comparative Example H:

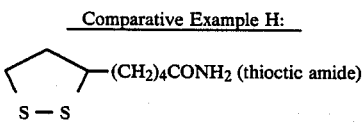

Moreover, as stated hereinbefore, we, the present inventors, have made further investigation to find out that when the new compound of the general formula (I) is added to feed and administered along with the feed to livestock animals such as cattle, poultry, cultivated fish and the like, the new compound is effective in reducing the internal fat accumulated and deposited within the animal bodies, especially, the abdominal fat without impairing the normal growth of the animals and/or the new compound is effective for the prevention of such excessive accumulation of the internal fat in the animal bodies. It has also been found that the new compound of this invention is effective in improving the efficiency of conversion of feed into edible meat proteins and the quality of the carcass as recovered from the livestock animals, owing to that the new compound can prevent the excessive accumulation of the internal fat.

In another aspect of this invention, there is thus provided an agent for reducing the internal fat or for preventing the excessive accumulation or deposit of the internal fat in the interior of the body of animals, including humans, which comprises a 1,3-dithiol-2-ylidene sulfonylacetate derivative of the general formula (I) as an active ingredient.

There is also provided a method for preventing or reducing an excessive accumulation or deposit of the internal fat in the interior of the body of animals, including humans, which comprises administering orally or parenterally an effective amount of a compound of the general formula

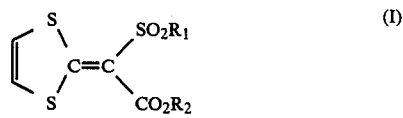

wherein $R_1$ and $R_2$ mean individually a lower alkyl group.

The compound of the general formula (I) according to the present invention, which is used as an active ingredient, can be formulated into a dosage form by mixing it with a solid or liquid carrier or vehicle. Since the compound of the general formula (I) is suitable for its incorporation in an animal feed, it may also be administered by admixing it uniformly with the animal feed so that its concentration ranges from 1 to 4,000 ppm, preferably, from 20 to 2,000 ppm. Components of the feed may vary widely in their kinds and proportions. The intended effects of the compound (I) of this invention are however not affected by the kinds of feed components. The fat reducing agent of this invention is effective for various animals. It may therefore be administered to poultry, e.g., chickens, turkeys, ducks and quails, and cattle, e.g., bovines, horses, swine, sheep and goats, as well as cultivated fish, e.g., yellow tails, carps and eels.

The internal fat-reducing agent of this invention is also expected to be effective for the prevention of overweight of men.

When employed as the fat reducing agents, the compounds (I) of the present invention also have superior effects to the known compounds of similar kinds, as will be demonstrated in subsequent Tests. Namely, the compound (I) of this invention can clearly reduce the amounts of the internal fat, especially, the abdominal fat of cattle, poultry and cultivated fish without inducing decrease in their normal body weight gains when it is added to feed and so administered to such animals. Each compound of this invention can clearly reduce the accumulated amount of abdominal fat and the fat content in the liver when it is added at a concentration of 400 ppm or so in the feed for its administration. The reduction in the fat contents in animal bodies can bring about profits to livestock farmers owing to the improved carcass quality and the improved efficiency of utilization of the carcass as meat, and moreover the low-fat meat of good quality so obtained can meet the consumer's demand for low-calorie diet foods. When employed as the fat-reducing agents, the compounds of this invention are also expected to achieve a significant contribution because the compounds of this invention are superior in their effects to the known similar compounds and are also advantageously more safe to men.

Various feed compositions may be formulated by admixing an internal fat-reducing agent comprising one or more of the compounds (I) of this invention as the active ingredient with the feed components. The formulation of such feed composition and the way of feeding such feed composition to the animals may vary depending on the kinds of cattle, poultry, cultivated fish and the like, their breeding or cultivating environment and conditions, their preference in taste, their manner of eating the feed, their sexes, their ages, and so on. It is hence impossible to specify them. Some feed compositions and the way of feeding the feed composition will however be described next by way of example.

As examples of livestock feed to which the internal fat-reducing agent of this invention can be added, may be mentioned corn, milo, rice, barley, rice bran, soybean cakes, fish meal and alfalfa meal. Illustrative examples of additives which can be incorporated into such feed may include calcium carbonate, calcium phosphate, table salt, choline chloride, vitamins such as vitamin A, vitamin D, vitamin K, vitamin $B_1$, vitamin $B_2$, vitamin $B_6$, vitamin $B_{12}$, pantothenic acid and methionine, inorganic salts such as copper sulfate, iron sulfate, magnesium, zinc sulfide and cobalt sulfate. Preventives for various diseases, for example, one or more of sulfa drugs, antibiotics and the like may also be chosen and added as needed. In many instances, such feed may take the form of mash or granules.

Among the livestock feed, chicken feed include broiler breeding feed, egg-producing feed (e.g., chick breeding feed and hen breeding feed), etc. They differ slightly from one another in their formulations but may be produced by choosing some of materials and small-quantity additives such as those described below and then blending them together for application. For instance, one or more of corn, milo, fish meal, fish soluble, safflower meal, corn gluten feed, soybean cakes, sesame cakes, defatted rice bran, bran, alfalfa meal and yeasts may be used as the principal components, with which one or more of the following additives may be admixed: the fermentative products, molasses, calcium and calcium compounds, phosphoric acid, choline, pantothenic acid, folic acid, manganese, zinc, salts, table salt, vitamin preparations, minerals, synthetic amino acids, yolk-coloring agents, antibiotics, antioxidants, preventives for various diseases, etc. These feed so formulated may be used in the form of mash in many instances.

Feed for cultivated fish can be produced by suitably choosing one or more animal-derived materials such as white fish meal, blood meal, liver powder, skim powder, defatted chrysalis meal and/or dried fish solubles as well as one or more vegetable-derived materials such as wheat flour, rice flour, processed rice bran, soybean cakes, gluten meal, yeasts, alfalfa meal, pregelatinized starch and activated wheat gluten and then blending them together. The feed so formulated may be in the form of grains such as pellets or granules.

The above mentioned feed for cattle, poultry, cultivated fish or the like may also contain, as needed, one or more principal materials and/or small-quantity additives other than those mentioned above. Their application forms are not necessarily limited to mash, pellets or granules. The feed compositions may be used in various forms in accordance with their application purposes.

Feed compositions containing some compound of the formula (I) added thereto will next be described by way of example. It should however be borne in mind that the present invention is not limited to the following Examples. In the following Examples, all designations of "part" or "parts" are given in part by weight or parts by weight.

EXAMPLE 16: FEED FOR HENS

Feed for hens was produced by uniformly admixing 0.04 part of Compound No. 13 (see Table 1) with 100 parts of "New Leghorn Hit" (trade mark; product of NISSHIN FLOUR MILLING CO., LTD.).

EXAMPLE 17: FEED FOR BROILERS

Feed for broilers was produced by uniformly admixing 0.04 part of Compound No. 16 (see Table 1) with 100 parts of "Broiler Starter" (trade mark, product of NIHON SHIRYO K.K.).

Each compound (I) of this invention may be added into a component of blended feed as above or may be mixed in a single-component feed.

The acute toxicity levels ($LD_{50}$) of Compound Nos. 13 and 16 shown in Table 1 were each 5,000 mg/kg or greater upon their oral administration to mice.

In summary, the compounds (I) of this invention have superior physiological activities to known compounds of similar kinds. First of all, the compounds of this invention exhibit the effects of controlling a variety of plant diseases such as rice blast (*Pyricularia oryzae*), rice sheath blight (*Rhizoctonia solani*), rice Helmintosporium leaf spot (*Cochliobolus miyabeanus*), rice seedling blight (*Fusarium roseum*) and rice "Bakanae" disease (*Gibberella fujikuroi*); vegetable powdery mildew (*Sphaerotheca fuliginea*), vegetable gray mold (*Botrytis cinerea*), vegetable scab (*Cladosporium cucumerinum*) and vegetable downy mildew (*Peronospora brassicea*); Brassicaceae clubroot (*Plasmodiophora brassicae*); beet damping-off (*Pythium debaryanum*) and beet Cercospora leaf spot (*Cercospora beticola*); and barley bunt (*Tilletia pancicii*) and barley scab (*Gibberella zeae*). Especially, the compounds of this invention show higher effects of controlling rice blast as well as barley and vegetable powdery mildew, all of which are considered to be very serious diseases, as compared to the known, similar compounds. The compounds of this invention can have far higher control effects against these diseases in the fields than the known compounds of similar kinds. Furthermore, it is also worthy to note that the compounds of this invention do not give any phyto-toxycity to crop plants even when sprayed at concentrations somewhat higher than their spray concentrations which are usually deemed as most suitable for the control of such diseases.

Secondly, the compounds of this invention are also useful as medicines, namely, as preventives or curing agents for hepatopathy. In other words, the compounds of this invention activate hepatocytes so as to regain the normal functions of the liver, such as glucosidic metabolism, detoxication, production and secretion of bile or bile acid, regeneration of hepatocytes, etc. They are also effective for damaged livers so that the liver damages can be either reduced or eliminated.

Thirdly, the compounds of this invention can be added to feed as the internal fat-reducing agents. When the resultant feed compositions are fed to cattle, poultry and cultivated fish, the compounds of this invention serve to reduce the amount of their abdominal fat without decreasing their normal body weight gain.

In order to demonstrate the effects of the fat reducing agents of this invention, Tests will be described hereinafter.

TEST 4:

To each group consisting of 30 "A,A Fuji" broilers (15 male, 15 female), commercial early-period broiler feed (crumble form, Cp 22%, ME, 3,030 kcal/kg) was given from the beginning of feeding to 4 week age, and a latter-period broiler feed (mash form, Cp 18%, ME 3,030 kcal/kg) was given ad libitum from the 4 week age to 10 week age.

Addition of the test compounds indicated in Table 5 below to the above feed compositions at predetermined concentrations and the administration of the test compound were conducted at the 3 week age and until the completion of the test.

The daily feed consumption per broiler was about 113 g. Hence, the total daily dose of each test compound per broiler was amounting to about 23 mg–about 362 mg.

STUDY ITEMS AND TESTING METHODS (a) Growth rate:

Body weight was measured at the beginning of feeding and every other week after the 3 week age. All broilers were measured individually and an average body weight was calculated for each group of broilers.

(b) Feed consumption:

Feed consumption was calculated by weighing the feed left over at the time of the body weight measurement, and therefrom the feed conversion ratio was calculated.

(c) Fat deposit:

Five broilers at 6 week age, five broilers at 8 week age and ten broilers at 10 week age were taken out from each group of broilers and slaughtered. Immediately after that, the sacrificed broilers were cooled in water for about 2 hours and the body weight of each slaughtered broiler was measured, and subsequently they were stored at 2° C. for about 20 hours. Then, in order to measure the amount of the abdominal fat (excluding the mesentery fat from measurement), the fat adhered and deposited on the gizzard and the proventriculus was collected and weighed as the weight of the abdominal fat. This weight was divided by the said body weight to evaluate the amount of the abdominal fat deposit per 100 g of the body weight. Further, liver fat was also collected and weighed. To this end, each liver sample under freeze storage was cut into slices in a total quantity of 2 to 3 g. The liver slices were placed in a cylindrical filter paper and weighed. Then, these slices were dried for 3 hours in a hot air drier maintained at 90° C. and subsequently extracted for 17 hours with ethyl ether in a Soxhlet fat extractor. After drying the extract solution for 3 hours at 60° C., the resultant fat residue was weighed to evaluate the crude fat content in the liver.

Test results are summarized in Tables 5 and 6. The tendency of slight reduction in the feed consumption was observed for the group of broilers fed with feed compositions containing 3,200 ppm of the compounds (I) of this invention. In the groups of broilers fed with feed compositions containing 800 ppm or more of Comparative Chemical A, a significantly reduced feed consumption was observed. A substantially reduced feed consumption was also observed in the groups fed with feed compositions containing 1,600 ppm and more of Comparative Chemical B, respectively.

TABLE 5

| Test compound No. | Compound concentration in feed (ppm) | Body Weight Gain — Broiler body weight (g) at each week age | | | | | | | | |
|---|---|---|---|---|---|---|---|---|---|---|
| | | 0 | 3 | 4 | 5 | 6 | 7 | 8 | 9 | 10 |
| 1 | 1600 | 41 | 624 | 981 | 1321 | 1688 | 2099 | 2480 | 2863 | 3125 |
| 2 | 1600 | 41 | 623 | 982 | 1327 | 1694 | 2104 | 2485 | 2862 | 3124 |
| 3 | 1600 | 41 | 622 | 984 | 1324 | 1697 | 2111 | 2490 | 2864 | 3126 |
| 4 | 1600 | 41 | 623 | 981 | 1321 | 1692 | 2105 | 2487 | 2858 | 3120 |
| 5 | 1600 | 41 | 623 | 982 | 1329 | 1694 | 2100 | 2478 | 2865 | 3121 |
| 6 | 1600 | 41 | 624 | 983 | 1328 | 1690 | 2103 | 2482 | 2863 | 3124 |
| 7 | 1600 | 41 | 625 | 981 | 1324 | 1693 | 2105 | 2483 | 2865 | 3120 |
| 8 | 1600 | 41 | 626 | 982 | 1324 | 1688 | 2102 | 2482 | 2861 | 3124 |
| 9 | 1600 | 41 | 624 | 981 | 1328 | 1689 | 2103 | 2485 | 2865 | 3126 |
| 10 | 1600 | 41 | 625 | 984 | 1326 | 1695 | 2108 | 2486 | 2863 | 3120 |
| 11 | 1600 | 41 | 623 | 982 | 1325 | 1691 | 2099 | 2480 | 2858 | 3124 |
| 12 | 1600 | 41 | 622 | 979 | 1320 | 1694 | 2097 | 2483 | 2862 | 3121 |
| 13 | 200 | 41 | 613 | 984 | 1330 | 1690 | 2105 | 2488 | 2863 | 3124 |
| 13 | 400 | 41 | 629 | 982 | 1325 | 1693 | 2108 | 2487 | 2868 | 3128 |
| 13 | 800 | 41 | 631 | 987 | 1326 | 1692 | 2102 | 2482 | 2868 | 3130 |
| 13 | 1600 | 41 | 626 | 986 | 1328 | 1690 | 2101 | 2480 | 2862 | 3129 |
| 13 | 3200 | 41 | 618 | 976 | 1310 | 1668 | 2071 | 2448 | 2825 | 3080 |
| 14 | 1600 | 41 | 625 | 984 | 1321 | 1697 | 2104 | 2487 | 2864 | 3128 |
| 15 | 1600 | 41 | 624 | 982 | 1324 | 1698 | 2108 | 2482 | 2862 | 3126 |
| 16 | 200 | 41 | 625 | 985 | 1326 | 1694 | 2106 | 2489 | 2861 | 3124 |
| 16 | 400 | 41 | 627 | 983 | 1328 | 1692 | 2103 | 2481 | 2860 | 3120 |
| 16 | 800 | 41 | 624 | 982 | 1326 | 1694 | 2098 | 2480 | 2859 | 3121 |
| 16 | 1600 | 41 | 628 | 984 | 1321 | 1693 | 2104 | 2483 | 2862 | 3124 |
| 16 | 3200 | 41 | 619 | 978 | 1312 | 1670 | 2075 | 2450 | 2829 | 3086 |
| 17 | 1600 | 41 | 624 | 986 | 1322 | 1692 | 2108 | 2487 | 2863 | 3125 |
| Comparative* Chemical A | 200 | 41 | 620 | 981 | 1320 | 1682 | 2090 | 2469 | 2845 | 3102 |
| Comparative* Chemical A | 400 | 41 | 618 | 974 | 1316 | 1664 | 2078 | 2441 | 2821 | 3087 |
| Comparative* Chemical A | 800 | 41 | 611 | 969 | 1301 | 1651 | 2054 | 2420 | 2792 | 3051 |

TABLE 5-continued

| Test compound No. | Compound concentration in feed (ppm) | Body Weight Gain Broiler body weight (g) at each week age | | | | | | | | |
|---|---|---|---|---|---|---|---|---|---|---|
| | | 0 | 3 | 4 | 5 | 6 | 7 | 8 | 9 | 10 |
| Comparative* Chemical A | 1600 | 41 | 609 | 960 | 1287 | 1643 | 2041 | 2403 | 2773 | 3033 |
| Comparative* Chemical A | 3200 | 41 | 605 | 954 | 1268 | 1622 | 2026 | 2389 | 2764 | 3018 |
| Comparative* Chemical B | 200 | 41 | 627 | 982 | 1328 | 1691 | 2105 | 2483 | 2858 | 3121 |
| Comparative* Chemical B | 400 | 41 | 623 | 980 | 1326 | 1690 | 2100 | 2480 | 2852 | 3119 |
| Comparative* Chemical B | 800 | 41 | 623 | 979 | 1322 | 1687 | 2086 | 2475 | 2846 | 3114 |
| Comparative* Chemical B | 1600 | 41 | 615 | 976 | 1310 | 1668 | 2070 | 2444 | 2821 | 3088 |
| Comparative* Chemical B | 3200 | 41 | 608 | 963 | 1298 | 1651 | 2051 | 2430 | 2803 | 3060 |
| Not added (untreated) | — | 41 | 623 | 983 | 1325 | 1690 | 2100 | 2481 | 2860 | 3121 |

*Comparative Chemical A:

[Structure: NC-C(S-)=C(S-)-NC with S-S bridge forming C=C(SO$_2$-C$_6$H$_4$-CH$_3$)(CO$_2$H)]

(Prepared newly by the present inventors with deducing from Claims 1 of U.S. Pat. No. 3,057,875.)

*Comparative Chemical B: (see Tables 2–3)

[Structure: cyclic dithio-C=C(CO$_2$C$_3$H$_7$-i)(CO$_2$C$_3$H$_7$-i)]

(Described in Japanese Patent Application first publication "Kokai" No. 34852/1984 or Japanese Patent Publication No. 34126/1972)

TABLE 6

| Test compound No. | Compound concentration in feed (ppm) | Fat Deposit Abdominal fat deposit (g/100 g) at each week age | | | Crude fat content in liver (%) at each week age | | |
|---|---|---|---|---|---|---|---|
| | | 6 | 8 | 10 | 6 | 8 | 10 |
| 1 | 400 | 2.98 | 3.19 | 3.30 | 2.08 | 4.24 | 4.20 |
| 2 | 400 | 2.99 | 3.21 | 3.28 | 2.10 | 4.28 | 4.19 |
| 3 | 400 | 2.99 | 3.22 | 3.27 | 2.07 | 4.27 | 4.21 |
| 4 | 400 | 3.01 | 3.20 | 3.29 | 2.08 | 4.26 | 4.23 |
| 5 | 400 | 3.00 | 3.24 | 3.31 | 2.12 | 4.22 | 4.22 |
| 6 | 400 | 2.97 | 3.19 | 3.28 | 2.10 | 4.19 | 4.19 |
| 7 | 400 | 2.98 | 3.18 | 3.29 | 2.08 | 4.23 | 4.20 |
| 8 | 400 | 2.99 | 3.18 | 3.30 | 2.09 | 4.19 | 4.21 |
| 9 | 400 | 3.04 | 3.22 | 3.31 | 2.06 | 4.27 | 4.21 |
| 10 | 400 | 3.02 | 3.23 | 3.29 | 2.08 | 4.23 | 4.18 |
| 11 | 400 | 3.06 | 3.21 | 3.26 | 2.07 | 4.24 | 4.20 |
| 12 | 400 | 3.05 | 3.21 | 3.28 | 2.10 | 4.21 | 4.21 |
| 13 | 200 | 3.08 | 3.25 | 3.36 | 2.14 | 4.41 | 4.51 |
| 13 | 400 | 2.98 | 3.18 | 3.24 | 2.06 | 4.23 | 4.21 |
| 13 | 800 | 2.96 | 3.18 | 3.23 | 2.06 | 4.21 | 4.18 |
| 13 | 1600 | 2.96 | 3.16 | 3.21 | 2.04 | 4.20 | 4.15 |
| 13 | 3200 | 2.94 | 3.15 | 3.20 | 2.02 | 4.20 | 4.10 |
| 14 | 400 | 2.98 | 3.18 | 3.26 | 2.08 | 4.22 | 4.20 |
| 15 | 400 | 2.99 | 3.20 | 3.25 | 2.09 | 4.25 | 4.22 |
| 16 | 200 | 3.06 | 3.23 | 3.32 | 2.13 | 4.38 | 4.42 |
| 16 | 400 | 2.96 | 3.16 | 3.21 | 2.04 | 4.20 | 4.18 |
| 16 | 800 | 2.94 | 3.15 | 3.18 | 2.03 | 4.18 | 4.15 |
| 16 | 1600 | 2.94 | 3.13 | 3.17 | 2.01 | 4.16 | 4.12 |
| 16 | 3200 | 2.92 | 3.10 | 3.16 | 2.01 | 4.15 | 4.07 |
| 17 | 400 | 3.00 | 3.20 | 3.28 | 2.00 | 4.21 | 4.21 |
| Comparative* Chemical A | 200 | 3.33 | 3.96 | 4.43 | 2.28 | 5.89 | 5.48 |
| Comparative* Chemical A | 400 | 3.34 | 3.98 | 4.43 | 2.32 | 5.94 | 5.48 |
| Comparative* Chemical A | 800 | 3.32 | 4.01 | 4.48 | 2.36 | 6.02 | 5.57 |
| Comparative* Chemical A | 1600 | 3.33 | 4.03 | 4.52 | 2.41 | 6.13 | 5.68 |
| Comparative* Chemical A | 3200 | 3.35 | 4.06 | 4.58 | 2.48 | 6.26 | 5.89 |
| Comparative* Chemical B | 200 | 3.18 | 3.87 | 3.93 | 2.24 | 5.46 | 5.36 |

TABLE 6-continued

| Test compound No. | Compound concentration in feed (ppm) | Fat Deposit Abdominal fat deposit (g/100 g) at each week age | | | Crude fat content in liver (%) at each week age | | |
| --- | --- | --- | --- | --- | --- | --- | --- |
| | | 6 | 8 | 10 | 6 | 8 | 10 |
| Comparative* Chemical B | 400 | 3.10 | 3.62 | 3.77 | 2.18 | 4.98 | 4.95 |
| Comparative* Chemical B | 800 | 2.98 | 3.15 | 3.24 | 2.06 | 4.22 | 4.20 |
| Comparative* Chemical B | 1600 | 2.96 | 3.13 | 3.20 | 2.04 | 4.20 | 4.18 |
| Comparative* Chemical B | 3200 | 2.98 | 3.14 | 3.22 | 2.08 | 4.20 | 4.17 |
| Not added (untreated) | — | 3.33 | 3.94 | 4.42 | 2.28 | 5.84 | 5.43 |

*see Table 5.

As apparent from the results shown in Table 5, slight inferiority in the growth of broilers was observed with significance only in the groups of broilers fed with feed compositions containing 3,200 ppm of the compounds (I) of this invention. In the groups of broilers receiving the compounds at the other concentrations, the body weight gain increased as much as in the untreated groups of broilers. On the other hand, slight weight loss was observed in the group of broilers receiving the feed containing 400 ppm of Comparative Chemical A, and also a clear weight loss was found in the groups of broilers fed with feed compositions containing 800 ppm and more of Comparative Chemical B, respectively. This was closely related to the reduction in the feed consumption as induced during the test. The reduced body weight gain is evidently attributable to the reduction in the feed consumption. Since the compounds (I) of this invention do not reduce the normal body weight gain as demonstrated above, they are considered to be safer chemicals compared with the comparative chemicals. As clearly envisaged from Table 6, the amount of the abdominal fat deposit and the fat content in the liver are both reduced significantly when the compounds (I) of this invention are administered even at their concentrations in the feed as low as 400 ppm. In the case of Comparative Chemical A, no reduction was observed in the amount of the abdominal fat deposit in the entire groups of broilers under test. In the case of Comparative Chemical B, its concentration of about 800 ppm was required at least to achieve an apparent reduction in the amount of the abdominal fat deposit.

We claim:

1. A 1,3-dithiol-2-ylidene sulfonylacetate derivative of the formula

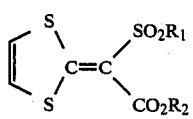

Wherein $R_1$ and $R_2$ mean individually a lower alkyl group.

2. A derivative as claimed in claim 1 in which a lower alkyl group for $R_1$ and $R_2$ is selected from methyl, ethyl, n-propyl, iso-propyl, n-butyl, iso-butyl, tertbutyl, pentyl and hexyl.

3. A derivative as claimed in claim 1, which is ethyl 1,3-dithiol-2-ylidene-isopropylsulfonyl acetate or methyl 1,3-dithiol-2-ylidene-n-butylsulfonylacetate.

4. A fungicidal composition for agricultural and horticultural utility, comprising, as an active ingredient, a 1,3-dithiol-2-ylidene sulfonylacetate derivative of the formula:

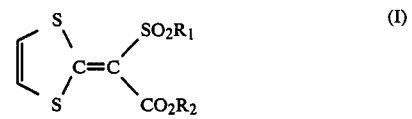

wherein $R_1$ and $R_2$ mean individually a lower alkyl group in combination with a solid or liquid carrier for the active ingredient.

5. A method for therapeutically treating or preventing a liver disorder of animals, including humans, which comprises orally or parenterally administering to said animal in need of the therapy or prevention, an effective amount of a compound of the formula

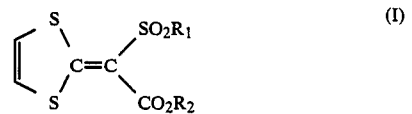

wherein $R_1$ and $R_2$ mean individually a lower alkyl group.

6. A method for preventing or reducing an excessive accumulation or deposit of the internal fat in the interior of the body of animals, including humans, which comprises administering orally or parenterally an effective amount of a compound of the formula

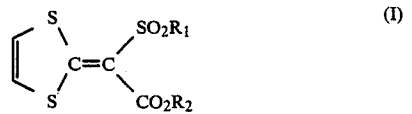

wherein $R_1$ and $R_2$ mean individually a lower alkyl group.

* * * * *